US006306894B1

(12) United States Patent
Carver et al.

(10) Patent No.: US 6,306,894 B1
(45) Date of Patent: *Oct. 23, 2001

(54) INJECTABLE COMPOSITION

(75) Inventors: David Carver, Boulder; Timothy Prout, Erie; Hernita Ewald, Denver, all of CO (US); Robyn Elliott, Langwarrin; Paul Handreck, Glen Iris, both of (AU)

(73) Assignee: NaPro Biotherapeutics, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/563,969

(22) Filed: May 3, 2000

Related U.S. Application Data

(63) Continuation of application No. 09/356,158, filed on Jul. 19, 1999, now Pat. No. 6,140,359, which is a continuation of application No. 08/979,836, filed on Nov. 26, 1997, now Pat. No. 5,977,164, which is a division of application No. 08/594,478, filed on Jan. 31, 1996, now Pat. No. 5,733,888, which is a continuation of application No. 07/995,501, filed on Dec. 22, 1992, now abandoned.

(30) Foreign Application Priority Data

Nov. 27, 1992 (AU) .......................................... 6074

(51) Int. Cl.$^7$ ................................................. A61K 31/335
(52) U.S. Cl. .............................................................. 514/449
(58) Field of Search .............................................. 911/444

(56) References Cited

U.S. PATENT DOCUMENTS

| | | | |
|---|---|---|---|
| 3,864,370 | 2/1975 | Yamashito et al. . | |
| 4,814,470 | 3/1989 | Colin et al. | 514/449 |
| 4,942,184 | 7/1990 | Haugwitz et al. | 414/449 |
| 4,960,790 | 10/1990 | Stella et al. | 519/449 |
| 5,157,049 | 10/1992 | Haugwitz et al. | 514/449 |
| 5,254,580 | 10/1993 | Chen et al. | 514/449 |
| 5,281,727 | 1/1994 | Carver et al. | 514/449 |
| 5,391,385 | 2/1995 | Seybold | 514/444 |
| 5,403,858 | 4/1995 | Bastard | 514/471 |
| 5,504,102 | 4/1996 | Agharkar et al. | 514/449 |
| 5,733,388 | 3/1998 | Carver et al. | 514/449 |

FOREIGN PATENT DOCUMENTS

| | | |
|---|---|---|
| 32861 | 1/1989 | (AU) . |
| 428376 | 5/1991 | (EP) . |
| 505047 | of 1992 | (EP) . |
| 522936 | of 1993 | (EP) . |
| 522937 | of 1993 | (EP) . |
| 9010443 | of 1990 | (WO) . |
| 9412198 | of 1994 | (WO) . |

OTHER PUBLICATIONS

Kingston, et al., "Synthesis and Structure–Activity Relationships of Taxol Derivatives as Anticancer Agents", Studies in Organic Chemistry 26:219–235, 1986.*

Dordunoo, Stephen K., and Helen M. Burt (1996) "Solubility and Stability of Taxol: Effects of Buffers and Cyclodextrins" International Journal of Pharmaceutics 133: 191–201.
Kingston, David G.I., Neal F. Magri, Chote Jitrangsri (1986) "Synthesis and Structure–Activity Relationships of Taxol Derivatives as Anticancer Agents" Studies in Organic Chemistry 26:219–235.
Kingston, David G. I. (1991) The Chemistry of Taxol: Pharmac. Ther. 52:1–34.
Longnecker, et al. (1987) "High Performance Liquid Chromatographic Assay of Taxol in Human Plasma and Pharmacokitetics in Phase I Trial" Cancer Treatment Reports 71(1).
Magri, Neal F. and David G. I. Kingston (1986) "Modified Taxols. 2. Oxidation Products of Taxol" Journal of Org. Chem. 51:797–802.
Mathew, A. E. M. Mejillano, J. P. Nath, R. H. Himes, and V. J. Stella (1992) "Synthesis and Evaluation of Some Water Soluble Prodrugs and Derivat ives of Taxol and Antitumor Activity," J. Med. Chem. 35:145–51.
Richheimer, Steven L., David M. Tinnermeier and Daniel W. Timmons (1992) "High Performance Liquid Chromatographic Assay of Taxol" Anal Chem. 64:2323–2326.
Ringel, Israel, Susan Band Horwitz (1987) "Taxol is Converted to 7–Epitaxol, a Biologically Active isomer, in Cell Culture Medium" Journal of Pharmacology and Experimental therapeutics 242(1):692–698.
Waugh, Wanda n., Lawrence A. Trissel and Valentino J. Stella (1991) "Stability, Compatibility, and Plasticizer Extraction of Taxol (NCS–125973) Injection Diluted in infusion Solutions and Stored in Various Containers" Reports Taxol 48 1520–1524.
Rowinsky, E., et al. "Taxol: A Novel Investigational Antimicrotubule Agent" Journal of the National Cancer Institute (1990) 82(15): 1247–59.
Tarr, B. D. et al. "A New Parenteral Vehicle for the Administration of Some Poorly Soluble Anti–Cancer Drugs" J. Parenter. Sci. Technol. (1987) 41(1):31–33.
Trissel, Lawrence (1988) "Monographs on Digoxin, Edrophonium chloride, Etoposide, Hydromorphine Hcl, Methyldopate HC1, Metronidazole, Nalbupine HC2, Phenylephjrine HCl, and Vitamin A" Handbook on Injectable Drugs, 5$^{th}$ Edition.

* cited by examiner

Primary Examiner—Dwayne C. Jones
(74) Attorney, Agent, or Firm—Saliwanchik, Lloyd & Saliwanchik

(57) ABSTRACT

A pharmaceutical formulation of paclitaxel and polyethoxylated castor oil is disclosed to be relatively acidified to a pH of less than 8.1 and preferably within a pH range of 5 to 7, inclusively. Ethanol is optionally included in the formulation which is adapted for use in a body for the treatment of cancer. A formulation method is disclosed and includes the step of mixing an acid with a carrier material, such as polyethoxylated castor oil, to form a carrier solution after which paclitaxel is added in an amount such that the resulting pH is less than 8.1 and preferably in a pH range of 5 to 7. Ethanol may optionally be slurried with the paclitaxel before mixing with the carrier solution. A variety of acidifying agents, a preferred one being anhydrous citric acid, are described.

38 Claims, No Drawings

INJECTABLE COMPOSITION

CROSS-REFERENCE TO RELATED APPLICATIONS

This application is a continuation of U.S. Ser. No. 09/356,158, filed Jul. 19, 1999, now U.S. Pat. No. 6,140,359, which is a continuation of U.S. Ser. No. 08/979,836, filed Nov. 26, 1997, now U.S. Pat. No. 5,977,164, which is a divisional of U.S. Ser. No. 08/594,478, filed Jan. 31, 1996, now U.S. Pat. No. 5,733,888; which is a continuation of U.S. Ser. No. 07/995,501, filed Dec. 22, 1992, now abandoned.

This invention relate to a solution of paclitaxel having improved stability.

CROSS-REFERENCE TO RELATED FOREIGN APPLICATION

This application claims priority under 35 USC 119 to Australian Patent No. 6074 filed Nov. 27, 1992.

BACKGROUND OF THE INVENTION

Paclitaxel is a compound extracted from the bark of a western yew, *Taxus brevifolia* and known for its antineoplastic activity. It is described for example in The Merck Index, Eleventh Edition 1989, monograph 9049.

In 1977, paclitaxel was chosen for development as an antineoplastic agent because of its unique mechanism of action and good cytotoxic activity against IP implanted D16 melanoma and the human X-1 mammary tumor xenograft. Paclitaxel is believed to function as a mitotic spindle poison and as a potent inhibitor of cell replication in vitro. Other mitotic spindle points (colchicine and podophyllotoxin) inhibit microtubule assembly. Paclitaxel employs a different mechanism of action since it appears to shift the equilibrium of polymerimization/depolymerization toward polymer assembly and to stabilize microtubules against depolymerization under conditions which would cause rapid disaggregation of microtubules. The interference with the polymerization/depolymerization cycle in cells appears to interfere with both the replication and migration of cells.

After extensive preclinical screening in mouse tumor models, paclitaxel entered clinical trials in 1983. Over the past few years, paclitaxel has demonstrated good response rates in treating both ovarian and breast cancer patients who were not benefitting from vinca alkaloid or cisplatin therapy. It has also shown encouraging results in patients with other types of cancer including lung, melanoma, lymphoma, head and neck.

For further information, reference may be made to the U.S. National Cancer Institute's Clinical Brochure for Taxol, revised July 1991, and papers presented at the Second National Cancer Institute Workshop on Taxol and Taxus held in Alexandria, Va. USA on Sep. 23–24, 1992.

BRIEF DESCRIPTION OF THE INVENTION

It is a disadvantage of the known formulation that the paclitaxel therein degrades, with the result that the shelf life of the formulation is unsatisfactory, and there is therefore a need for a paclitaxel solution of improved stability.

Accordingly, in a general aspect the invention provides a solution containing paclitaxel, cremophor EL™ and ethanol, characterized in that the pH of the solution has been adjusted into the range 1 to 8 by addition of an acid.

Acids in the form of powders, for example citric acid, are preferred over those which contain water, for example sulfuric acid. The most preferred acid for use in accordance with the present invention is citric acid, but a wide range of acids may be used including the following:

Citric acid—monohydrous
Citric acid—anhydrous
Citric acid—hydrous
Acetic acid
Formic acid
Ascorbic acid
Aspartic acid
Benzene sulphonic acid
Benzoic acid
Hydrochloric acid
Sulphuric acid
Phosphoric acid
Nitric acid
Tartaric acid
Diatrizoic acid
Glutamic acid
Lactic acid
Maleic acid
Succinic acid

DETAILED DESCRIPTION OF THE ILLUSTRATED EMBODIMENTS

Due to its limited solubility in water, Paclitaxel is usually prepared and administered in a vehicle containing cremophor EL™ (a polyethoxylated castor oil which acts as a solubilizer) and ethanol. A commercially available solution supplied by Bristol-Myers Squibb (BMS) is formulated with these components and has a pH of 9.1.

As indicated above, the invention essentially teaches addition of an acid to a paclitaxel formulation to adjust its pH into the range 1 to 8, preferable 5 to 7.

In a preferred procedure adopted by the applicant, which it will be clearly understood is non-limiting, the following steps were carried out:

Mixing Instructions

Solution 1

Citric acid was dissolved in absolute alcohol, using a ratio of 8 mls of absolute alcohol to 1 gram of citric acid, and the solution was stirred for fifteen (15) minutes.

Solution 2

Cremophor EL was weighed out into the main mixing vessel.

Solution 3

Solution 1 was added to solution 2, and the container used for solution 2 was washed with a minimum quantity of absolute alcohol to ensure complete transfer of the citric acid. Solution 3 was mixed and bubbled with nitrogen for at least 15 minutes. The paclitaxel was weighed out and slurried using absolute alcohol, using a ratio of 8 ml of absolute alcohol to 1 gm of paclitaxel. The slurried paclitaxel was added to solution 3 and the slurrying vessel was washed with a minimum quantity of absolute alcohol. Solution 3 was adjusted to 75% of required volume using absolute alcohol, and thoroughly stirred for at least 45 minutes until completely dissolved. Once completely dissolved, the volume was checked and made up as necessary with absolute alcohol and the final solution stirred for 5 minutes.

EXAMPLE 1

A solution was prepared with the following formulation:

Formulation: (Sample 1)

| | |
|---|---|
| Cremophor EL | 0.5 mL |
| Citric Acid (Anhydrous) | 2.0 mg |
| Paclitaxel | 6.0 mg |
| Absolute Alcohol | to 1.0 mL |

The pH of this solution was determined as 6.1.

The stability of this sample was compared with a sample prepared by the formulation stated in the NCI Taxol Clinical brochure (as follows) which had a pH of 9.1. (Sample 2)

| Sample 2 | per mL |
|---|---|
| Paclitaxel | 6 mg |
| Cremophor EL | 0.5 mL |
| Absolute Alcohol | to 1 mL |

The solutions were filled into clear type 1 glass 5 mL vials and sealed with rubber bungs.

The solutions were stored at 40° C. for 7 (seven) days and the stability results are shown in Table 1.

| | Sample 1 | Sample 2 |
|---|---|---|
| pH | 6.2 | 9.0 |
| Potency | 96.6 | 86.7 |
| Major individual impurity | 0.3% | 5.1% |
| Total impurities | 1.0% | 12.2% |

Clearly Sample 1 showed significantly increased stability over Sample 2.

EXAMPLE 2

A solution was prepared with the following formulation:

Formulation: (Sample 3)

| | |
|---|---|
| Cremophor EL | 0.5 mL |
| Paclitaxel | 6.0 mg |
| Absolute Ethanol | to 1.0 mL |

The solution was filled into clear type I glass 5 mL vials and sealed with rubber bungs.

The solution was stored at 40° C. for 7 days.

The stability results obtained are compared to those seen with Sample 2.

| | Sample 1 | Sample 2 |
|---|---|---|
| pH | 6.7 | 9.0 |
| Potency | 97.5 | 86.7 |
| Major individual impurity | 0.3% | 5.1% |
| Total impurities | 2.3% | 12.2% |

Again the significantly superior stability of the formulation according to the invention (Sample 3) is evident.

It will be clearly understood that the invention in its general aspects is not limited to the specific details referred to hereinabove.

What is claimed is:

1. A composition of matter comprising a sealable container and a pharmaceutical formulation contained therein; said pharmaceutical formulation comprising paclitaxel, a pharmaceutically-acceptable carrier, and an acid, said formulation being such that at least 95% of the paclitaxel potency is retained when said formulation is stored at 40° C. for seven days; and wherein said pharmateutical formulation has been sealed in said container for at least seven days.

2. A composition of matter produced by the process of:
   a) obtaining a sealable container;
   b) obtaining a pharmaceutical formulation comprising paclitaxel, a pharmaceutically-acceptable carrier, and an acid, said formulation being such that at least 95% of the paclitaxel potency is retained when said formulation is stored at 40° C. for seven days;
   c) placing said pharmaceutical formulation in said sealable container;
   d) sealing said sealable container; and
   e) storing said pharmaceutical formulation in said sealed container for at least seven days.

3. A composition of matter according to claim 1, wherein said pharmaceutical formulation has a pH between 5 and 7, inclusive.

4. A composition of matter according to claim 1, further comprising ethanol as a constituent thereof.

5. A composition of matter according to claim 4, wherein said pharmaceutical formulation has a pH between 5 and 7, inclusive.

6. A composition of matter according to claim 1, wherein said pharmaceutically acceptable carrier is polyethoxylated castor oil.

7. A composition of matter according to claim 1, wherein said pharmaceutical formulation is anhydrous.

8. A composition of matter according to claim 6, wherein said acid is a mineral acid.

9. A composition of matter according to claim 6, wherein said acid is an organic acid.

10. A composition of matter according to claim 6, wherein said acid is acetic acid.

11. A composition of matter according to claim 6, wherein said acid is citric acid.

12. A composition of matter according to claim 11, wherein said citric acid is anhydrous.

13. A composition of matter according to claim 2, wherein said pharmaceutical formulation has a pH between 5 and 7, inclusive.

14. A composition of matter according to claim 2, further comprising ethanol as a constituent thereof.

15. A composition of matter according to claim 14, wherein said pharmaceutical formulation has a pH between 5 and 7, inclusive.

16. A composition of matter according to claim 2, wherein said pharmaceutically acceptable carrier is polyethoxylated castor oil.

17. A composition of matter according to claim 2, wherein said pharmaceutical formulation is anhydrous.

18. A composition of matter according to claim 16, wherein said acid is a mineral acid.

19. A composition of matter according to claim 16, wherein said acid is an organic acid.

20. A composition of matter according to claim 16, wherein said acid is acetic acid.

21. A composition of matter according to claim 16, wherein said acid is citric acid.

22. A composition of matter according to claim 21, wherein said citric acid is anhydrous.

23. A method of formulating a pharmaceutical paclitaxel composition such that the paclitaxel does not readily degrade, comprising the following steps:

mixing paclitaxel with a pharmaceutically acceptable carrier material to form a pharmaceutical paclitaxel composition, the pH of said carrier material having been reduced to a level such that when paclitaxel is mixed therewith at least 95% of the paclitaxel potency is retained when the composition is stored at 40° C. for seven days;

sealing said pharmaceutical paclitaxel composition in a sealable container; and storing said pharmaceutical paclitaxel composition in said sealed container for at least seven days.

24. A method according to claim 23, wherein said pharmaceutically acceptable carrier material comprises polyethoxylated castor oil.

25. A method according to claim 23, wherein said pharmaceutical paclitaxel composition is anhydrous.

26. A method according to claim 24, wherein said pharmaceutical paclitaxel composition also comprises ethanol.

27. An article of manufacture comprising a container and a pharmaceutical formulation contained therein, said pharmaceutical formulation comprising a pharmaceutically acceptable carrier and paclitaxel, wherein the pH of said pharmaceutically acceptable carrier has been reduced to a level such that at least 95% of the potency of paclitaxel added thereto is retained when the pharmaceutical formulation is stored at 40° C. for seven days.

28. An article of manufacture according to claim 27, wherein said pharmaceutically acceptable carrier comprises polyethoxylated castor oil.

29. An article of manufacture according to claim 28, wherein said pharmaceutical formulation is anhydrous.

30. An article of manufacture according to claim 28, wherein said pharmaceutical formulation further comprises ethanol.

31. A method of making a pharmaceutical paclitaxel composition, comprising the steps of:

obtaining a pharmaceutically acceptable carrier material;

reducing the pH of said carrier material to a level such that when paclitaxel is mixed therewith, at least 95% of the paclitaxel potency is retained when the resulting composition is stored at 40° C. for seven days;

mixing paclitaxel with said reduced-pH carrier material to form a pharmaceutical paclitaxel composition;

sealing said pharmaceutical paclitaxel composition in a sealable container; and storing said pharmaceutical paclitaxel composition in said sealed container for at least seven days.

32. A method according to claim 31, wherein said pharmaceutically acceptable carrier material comprises polyethoxylated castor oil.

33. A method according to claim 32 wherein said pharmaceutical paclitaxel composition is anhydrous.

34. A method according to claim 31, wherein said pharmaceutical paclitaxel composition further comprises ethanol.

35. A composition of matter produced by the process of:

obtaining a pharmaceutically acceptable carrier material;

reducing the pH of said carrier material to a level such that when paclitaxel is mixed therewith, at least 95% of the paclitaxel potency is retained when the resulting composition is stored at 40° C. for seven days;

mixing paclitaxel with said reduced-pH carrier material to form a pharmaceutical paclitaxel composition;

sealing said pharmaceutical paclitaxel composition in a sealable container; and storing said pharmaceutical paclitaxel composition in said sealed container for at least seven days.

36. A composition of matter according to claim 35 wherein said pharmaceutically acceptable carrier material comprises polyethoxylated castor oil.

37. A composition of matter according to claim 36, wherein said pharmaceutical paclitaxel composition is anhydrous.

38. A composition of matter according to claim 35, wherein said pharmaceutical paclitaxel composition further comprises ethanol.

* * * * *

UNITED STATES PATENT AND TRADEMARK OFFICE
CERTIFICATE OF CORRECTION

PATENT NO. : 6,306,894 B1
DATED : October 23, 2001
INVENTOR(S) : David Carver et al.

It is certified that error appears in the above-identified patent and that said Letters Patent is hereby corrected as shown below:

Column 1,
Line 13, "relate" should be -- relates --.
Line 36, "polymerimization" should be -- polymerization --.

Column 3,
Lines 47-48, insert -- pH adjusted to 6.6 with 1.0M Acetic Acid --.
Line 56, "Sample 1" should read -- Sample 3 --.

Column 4,
Line 8, "pharmateutical" should be -- pharmaceutical --

Signed and Sealed this

Thirteenth Day of August, 2002

*Attest:*

JAMES E. ROGAN
*Director of the United States Patent and Trademark Office*

*Attesting Officer*